United States Patent [19]

Hoyles

[11] 4,212,856

[45] Jul. 15, 1980

[54] TOOTHPASTE

[75] Inventor: Ronald Hoyles, Epsom Downs, England

[73] Assignee: Lever Brothers Company, New York, N.Y.

[21] Appl. No.: 965,727

[22] Filed: Dec. 1, 1978

[30] Foreign Application Priority Data

Dec. 7, 1977 [GB] United Kingdom ............... 50945/77

[51] Int. Cl.$^2$ .......................... A61K 7/16; A61K 7/18
[52] U.S. Cl. ......................................... 424/52; 424/49
[58] Field of Search ..................................... 424/49–58

[56] References Cited

U.S. PATENT DOCUMENTS

| | | | |
|---|---|---|---|
| 2,010,910 | 8/1935 | Atkins | 424/49 |
| 2,550,207 | 4/1951 | Tainter et al. | 424/49 |
| 3,060,098 | 10/1962 | Gershon | 424/57 |
| 3,957,968 | 5/1976 | Cordon | 424/57 |
| 4,060,599 | 11/1977 | Cordon | 424/49 |
| 4,098,878 | 7/1978 | Baines et al. | 424/52 |
| 4,118,471 | 10/1978 | Pensak | 424/52 |
| 4,123,517 | 10/1978 | Baines et al. | 424/57 |

*Primary Examiner*—Shep K. Rose
*Attorney, Agent, or Firm*—Melvin H. Kurtz

[57] ABSTRACT

The invention relates to a highly effective anti-caries toothpaste containing sodium monofluorophosphate and alumina trihydrate abrasive. The toothpaste has a dentine abrasion value of 30 to 60 units and the alumina trihydrate consists of a mixture of an alumina trihydrate of average particle size 5 to 13 microns and an alumina trihydrate having an average particle size below 1 micron, the two grades of alumina trihydrate being employed in a weight ratio of 30:70 to 70:30.

5 Claims, No Drawings

TOOTHPASTE

This invention relates to toothpastes and more particularly to toothpastes for combatting dental caries and which contain sodium monofluorophosphate (MFP) as anti-caries agent.

Many different formulations of MFP-containing toothpastes have been described, especially in the patent literature, and a number have been subjected to clinical testing. Generally speaking, the main difference between the various known MFP-containing toothpastes resides in the nature of the abrasive cleaning agent. In this regard, compatibility between the cleaning agent and the MFP is important since substantial loss of available MFP on storage of the product would obviously result in a inferior or ineffective product.

One of the abrasive cleaning agents for MFP-containing toothpastes that has more recently been employed in commercial products has been alumina trihydrate. Alumina trihydrate has very good compatibility with MFP. Clinical trial data for toothpastes containing alumina trihydrate as abrasive and 0.8% and 2% MFP are reported by, respectively, Andlaw, R. J. and Tucker, G. J., Brit. Dent. J., 1975, 138, 426–32 and by James, P. M. C. et al, Com. Dent. Oral. Epid., 1977, 5, 67–72. These toothpastes contained around 50% by weight of alumina trihydrate having an average particle size of about 16 microns. They gave satisfactory reduction in dental caries.

We have now discovered that an unexpectedly high degree of anti-caries effectiveness is exhibited by a toothpaste containing MFP and alumina trihydrate abrasive, when the abrasive imparts to the toothpaste a dentine abrasion value of 30 to 60 units, preferably 40 to 60 units, and consists of a mixture of (A) an alumina trihydrate having an average particle size of from 5 to 13 microns; and
(B) an alumina trihydrate having an average particle size of less than 1 micron, the weight ratio of (A) to (B) being from 30:70 to 70:30. The relative dentine abrasion of a toothpaste is measured according to the procedure given by the British Standards Institution in BS 5136:1974.

The total amount of alumina trihydrate is desirably from about 45% to about 55%, and preferably about 50%, by weight of the toothpaste.

The sub-micron alumina trihydrate may have an average particle size of 0.2 to 0.8 micron, particularly about 0.5 micron. It is produced commercially as a fine precipitate and not by grinding larger particles although it may be necessary to break-up any aggregates of the crystals that may be formed during the precipitation process. The other alpha-alumina trihydrate preferably has an average particle size of 5.5 to 7.5 microns. Alumina trihydrates of average particle size 5 to 13 microns are generally produced commercially by grinding much larger sized particles produced in the Bayer process.

The amount of MFP is preferably used in the conventional amount of about 0.8% by weight of the toothpaste but other effective amounts such as in the range of 0.5 to 2.5% may also be used.

The other ingredients of the toothpaste will be conventional ingredients. Thus the toothpaste will usually comprise an humectant, for example glycerol or sorbitol, surface active agent, binding agent and flavouring agent. Other agents commonly included are sweetening agent, whitening agent, preservative and germicide. The pH of the toothpaste is desirably between 5.5 and 8.5.

The good reductions in caries incidence through the use of the above-described toothpaste are obtained in the absence of zinc ion-producing anti-plaque agents, such as zinc citrate.

An example of a toothpaste according to the invention will now be given. Percentages are by weight.

EXAMPLE

|  | % |
|---|---|
| Alpha-alumina trihydrate (aps 6.5 microns) | 22.5 |
| Alpha-alumina trihydrate (aps 0.5 micron) | 27.5 |
| Sorbitol syrup | 27.0 |
| Sodium carboxymethylcellulose | 1.1 |
| Sodium lauryl sulphate | 1.5 |
| Sodium monofluorophosphate | 0.8 |
| Titanium dioxide | 0.5 |
| Sodium saccharin | 0.3 |
| Flavouring | 1.0 |
| Sodium dihydrogen phosphate | 0.3 |
| Benzoic acid | 0.2 |
| Water | to 100.0 |
| pH 6.5 to 7.5 | |

(aps = average particle size)

The toothpaste had a relative dentine abrasion of 50 units.

Toothpaste of the above formula has been clinically tested along with a placebo paste which was also of the above formula save that it contained no sodium monofluorophosphate and, as a positive control, a standard commercial product containing an alumina trihydrate abrasive (53%) of average particle size about 16 microns and sodium monofluorophosphate (0.8%). The standard commercial product had the same formula as that tested by Andlaw and Tucker; its relative dentine abrasion was 100 units. The higher dentine abrasion value of the standard product indicates that it was more effective in cleaning the teeth than the test product although both have adequate cleaning power.

The increments of caries occurring during the clinical test are indicated below both by the commonly used DMFS and DMFSU increments and by the more recently employed ECSI value (Wagg, B. J., Com. Dent. Oral Epid., 1974, 2, 219–24). The letters DMFS stand for "Decayed, Missing and Filled Surfaces", DMFSU is the DMFS value related to teeth erupting during the trial, and the letters ECSI stand for "Extrapolated Carious Surface Increment".

The nett increments over three years for these indices were as indicated in Table 1.

Table 1

|  | Toothpaste of the Invention | Positive Control | Placebo |
|---|---|---|---|
| DMFS | 4.22 | 4.72 | 6.43 |
| DMFSU | 0.93 | 1.20 | 1.58 |
| ECSI | 6.65 | 7.54 | 10.45 |

The numbers of children in the groups using the three toothpastes in Table 1 were 367, 383 and 356, respectively.

The comparison between pairs of toothpastes is given in Table 2.

Table 2

|  | Toothpaste of the Invention v Placebo | | Toothpaste of the Invention v Positive Control | | Positive Control v Placebo | |
| --- | --- | --- | --- | --- | --- | --- |
|  | Difference between Caries increments | % Difference | Difference between Caries increments | % Difference | Difference between Caries increments | % Difference |
| DMFS | 2.21**** | 34.4 | 0.51* | 10.7 | 1.71**** | 26.6 |
| DMFSU | 0.65**** | 41.2 | 0.27** | 22.8 | 0.38*** | 23.9 |
| ECSI | 3.80**** | 36.4 | 0.89* | 11.8 | 2.91**** | 27.9 |

Where
*indicates significance at $P < 0.2$
**indicates significance at $P < 0.05$
***indicates significance at $P < 0.01$
****indicates significance at $P < 0.001$ For comparison the results for the Andlaw and Tucker three year study are given in Table 3.

Table 3

|  | Caries Increments | | Caries Reduction | |
| --- | --- | --- | --- | --- |
|  | Test Toothpaste (same as Positive Control above) | Placebo | Difference between Caries increments | % Difference |
| DMFS | 7.14 | 8.81 | 1.67**** | 18.9 |
| DMFSU | 1.47 | 2.03 | 0.56**** | 27.6 |
| ECSI | 10.72 | 13.02 | 2.30**** | 17.6 |

The results show that the toothpaste of the invention gave a very high percentage caries reduction which exceeded that of the control toothpaste also containing an alumina trihydrate abrasive and sodium monofluorophosphate.

What is claimed is:

1. An anti-caries toothpaste containing sodium monofluorophosphate and alumina trihydrate abrasive, wherein the abrasive imparts to the toothpaste a dentine abrasion value of 30 to 60 units and consists of a mixture of
(A) an alumina trihydrate having an average particle size of from 5 to 13 microns; and
(B) an alumina trihydrate having an average particle size of less than 1 micron,
the weight ratio of (A) to (B) being from 30:70 to 70:30.

2. A toothpaste as claimed in claim 1, wherein alumina trihydrate (A) has an average particle size of 5.5 to 7.5 microns.

3. A toothpaste as claimed in claim 1, wherein alumina trihydrate (B) has an average particle size of 0.2 to 0.8 micron.

4. A toothpaste as claimed in claim 2, wherein alumina trihydrate (B) has an average particle size of 0.2 to 0.8 micron.

5. A toothpaste as claimed in claim 1, wherein the total amount of alumina trihydrate is 45 to 55% by weight of the toothpaste.

* * * * *